US006890956B2

(12) United States Patent
Churcher et al.

(10) Patent No.: US 6,890,956 B2
(45) Date of Patent: May 10, 2005

(54) CYCLOHEXYL SULPHONES AS GAMMA-SECRETASE INHIBITORS

(75) Inventors: Ian Churcher, Great Dunmow (GB); Timothy Harrison, Great Dunmow (GB); Sonia Kerrad, Huningue (FR); Alan John Nadin, Sawbridgeworth (GB); Andrew Pate Owens, Huntingdon (GB); Duncan Edward Shaw, Bishops Stortford (GB); Joanne Thomson, Bishops Stortford (GB); Susannah Williams, Basingstoke (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 0 days.

(21) Appl. No.: 10/679,902

(22) Filed: Oct. 6, 2003

(65) Prior Publication Data

US 2004/0121995 A1 Jun. 24, 2004

(30) Foreign Application Priority Data

Oct. 4, 2002 (GB) .............................................. 0223038

(51) Int. Cl.$^7$ ........................ A61K 31/18; C07C 323/23
(52) U.S. Cl. ......................................... 514/602; 564/85
(58) Field of Search .............................. 514/602; 564/85

(56) References Cited

U.S. PATENT DOCUMENTS

| 2,802,013 A | 8/1957 | Dodson |
| 2,812,330 A | 11/1957 | Dodson |

FOREIGN PATENT DOCUMENTS

| EP | 0863134 | 9/1998 |
| WO | WO 00/50391 | 8/2000 |
| WO | WO 03/055850 | 7/2003 |
| WO | WO 03/059335 | 7/2003 |

OTHER PUBLICATIONS

L. Capuano, et al., "Cyclische S–Oxide", Chemische Berichte, vol. 112, pp. 1012–1022 (1979).

J.M. Decesare, et al.:, "Gamma–and Beta–epoxy sulfones. Formation of different ring–sized products upon reaction with CH3MgI or LiN[CH(CH$_3$)$_2$]$_2$", Canadian Journal of Chemistry., vol. 59, pp. 1415–1424 (1981).

O. Eisleb, "Neue Synthesen mittels Natriumamids", Berichte Der Deutschen Chemischen Gesellschaft, vol. 74, pp. 1433–1450 (1978).

J. Golinski, et al., "Reactions of Organic Anions; XVIV. Catalytic Two–Phase Alkylation of Benzyl Sulfones and Sulfonamides", SYNTHESIS, No. 6, pp. 461–463 (1979).

P. Kisanga, et al., "Development, Synthetic Scope, and Mechanistic Studies of the Palladium–Catalyzed Cycloisomerization of Functionalized 1,6–Dienes in the Presence of Silane", Journal of the American Chemical Society, vol. 122, No. 41, pp. 10017–10026 (2000).

C. Koradin, et al., "Cesium Catalyzed Addition of Nitriles to Alkynes", SYNLETT, No. 10, pp. 1452–1454 (2000).

T. Oyuyama, et al., "Flash Photolytic Generation of a Dithio Carbocation from 1,3–Dithiolance Derivatives and Its Reaction with Nucleophiles", Bulletin of the Chemical Society of Japan, vol. 64, No. 9, pp. 2751–2756 (1991).

M. Makosza, et al., "Ambiphilic Reactivity of 2,4–Dinitrobenzyl p–Tolyl Sulfone Carbanion", Polish Journal of Chemistry, vol. 72, pp. 1198–1201 (1998).

R. K. Norris, et al., "The Stereochemistry of the S$_{RN}$1 Reaction In Some Cyclohexane Derivatives", TETRAHEDRON, Vol. 38, No. 8, pp. 1051–1057 (1982).

*Primary Examiner*—Taofiq Solola
(74) *Attorney, Agent, or Firm*—John C. Todaro; Gavin M. Buchan; Melvin Winokur

(57) ABSTRACT

Compounds of formula I:

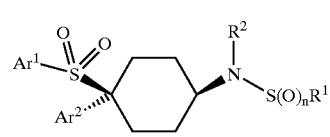

inhibit the processing of APP by gamma-secretase, and hence are useful in treating or preventing Alzheimer's disease.

9 Claims, No Drawings

CYCLOHEXYL SULPHONES AS GAMMA-SECRETASE INHIBITORS

CROSS-REFERENCE TO RELATED APPLICATIONS

This application claims priority under 35 U.S.C. § 119 from Great Britain application No. 0223038.1, filed Oct. 4, 2002.

The present invention relates to a novel class of compounds, their salts, pharmaceutical compositions comprising them, processes for making them and their use in therapy of the human body. In particular, the invention relates to novel cyclohexyl sulphones which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 00/50391 discloses a broad class of sulphonamides as modulators of the production of β-amyloid, but neither discloses nor suggests the compounds of the present invention.

The present invention provides a novel class of cyclohexyl sulphones which are useful in the treatment or prevention of AD by inhibiting the processing of APP by the putative γ-secretase, thus arresting the production of Aβ. The compounds of the invention generally combine a high affinity for the target enzyme with favourable pharmacokinetic properties.

According to the invention, there is provided a compound of formula I:

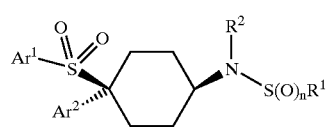

wherein n is 1 or 2;

$R^1$ represents $CF_3$ or $C_{1-6}$alkyl, $C_{2-6}$alkenyl, $C_{3-9}$cycloalkyl or $C_{3-6}$cycloalkyl$C_{1-6}$alkyl, any of which may bear up to 2 substituents selected from halogen, CN, $CF_3$, $OR^3$, $COR^3$, $CO_2R^3$, $OCOR^4$, $SO_2R^4$, $N(R^5)_2$, and $CON(R^5)_2$, or $R^1$ represents aryl, aryl$C_{1-6}$alkyl, C-heterocyclyl or C-heterocyclyl$C_{1-6}$alkyl;

$R^2$ represents H or $C_{1-4}$alkyl;

$R^3$ represents H, $C_{1-4}$alkyl, phenyl or heteroaryl;

$R^4$ represents $C_{1-4}$alkyl, phenyl or heteroaryl;

$R^5$ represents H or $C_{1-4}$alkyl, or two $R^5$ groups together with a nitrogen atom to which they are mutually attached complete an azetidine, pyrrolidine, piperidine, morpholine, thiomorpholine or thiomorpholine-1,1-dioxide ring;

$Ar^1$ and $Ar^2$ independently represent phenyl or heteroaryl, either of which bears 0–3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$acyl, $C_{2-6}$alkenyl and $C_{1-4}$alkyl which optionally bears a substituent selected from halogen, CN, $NO_2$, $CF_3$, OH and $C_{1-4}$alkoxy;

"aryl" at every occurrence thereof refers to phenyl or heteroaryl which optionally bear up to 3 substituents selected from halogen, CN, $NO_2$, $CF_3$, $OCF_3$, $OR^3$, $COR^3$, $CO_2R^3$, $OCOR^4$, $N(R^5)_2$, $CON(R^5)_2$ and optionally-substituted $C_{1-6}$alkyl, $C_{1-6}$alkoxy, $C_{2-6}$alkenyl or $C_{2-6}$alkenyloxy wherein the substituent is selected from halogen, CN, $CF_3$, phenyl, $OR^3$, $CO_2R^3$, $OCOR^4$, $N(R^5)_2$ and $CON(R^5)_2$; and "C-heterocyclyl" and "N-heterocyclyl" at every occurrence thereof refer respectively to a heterocyclic ring system bonded through carbon or nitrogen, said ring system being non-aromatic and comprising up to 10 atoms, at least one of which is O, N or S, and optionally bearing up to 3 substituents selected from oxo, halogen, CN, $NO_2$, $CF_3$, $OCF_3$, $OR^3$, $COR^3$, $CO_2R^3$, $OCOR^4$, $OSO_2R^4$, $N(R^5)_2$, $CON(R^5)_2$ and optionally-substituted phenyl, $C_{1-6}$alkyl, $C_{1-6}$alkoxy, $C_{2-6}$alkenyl or $C_{2-6}$alkenyloxy wherein the substituent is selected from halogen, CN, $CF_3$, $OR^3$, $CO_2R^3$, $OCOR^4$, $N(R^5)_2$ and $CON(R^5)_2$;

or a pharmaceutically acceptable salt thereof.

Where a variable occurs more than once in formula I, the individual occurrences are independent of each other, unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "$C_{3-9}$cycloalkyl" as used herein refers to nonaromatic monocyclic or fused bicyclic hydrocarbon ring systems comprising from 3 to 9 ring atoms. Examples include cyclopropyl, cyclobutyl, cyclopentyl, cyclohexyl, cyclohexenyl and bicyclo[2.2.1]heptyl. Monocyclic systems of 3 to 6 members are preferred.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "$C_{2-6}$acyl" as used herein refers to $C_{1-5}$alkylcarbonyl groups in which the alkyl portion may be straight chain, branched or cyclic, and may be halogenated. Examples include acetyl, propionyl and trifluoroacetyl.

The expression "heterocyclyl" as defined herein includes both monocyclic and fused bicyclic systems of up to 10 ring atoms selected from C, N, O and S. Mono- or bicyclic systems of up to 7 ring atoms are preferred, and monocyclic systems of 4, 5 or 6 ring atoms are most preferred. Examples of heterocyclic ring systems include azetidinyl, pyrrolidinyl, 3-pyrrolinyl, tetrahydrofuryl, 1,3-dioxolanyl, tetrahydrothiophenyl, tetrahydropyridinyl, piperidinyl, piperazinyl, morpholinyl, thiomorpholinyl, imidazolidinyl, oxazolidinyl, thiazolidinyl, 2,5-diazabicyclo[2.2.1]heptyl, 2-aza-5-oxabicyclo[2.2.1]heptyl and 1,4-dioxa-8-azaspiro

[4.5]decanyl. Unless otherwise indicated, heterocyclyl groups may be bonded through a ring carbon atom or a ring nitrogen atom where present. "C-heterocyclyl" indicates bonding through carbon, while "N-heterocyclyl" indicates bonding through nitrogen.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Monocyclic systems of 5 or 6 members are preferred. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine. Pyridine rings may be in the N-oxide form.

Where a phenyl group or heteroaryl group bears more than one substituent, preferably not more than one of said substituents is other than halogen or alkyl. Where an alkyl group bears more than one substituent, preferably not more than one of said substituents is other than halogen.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, benzenesulfonic acid, methanesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, n is 1 or 2, preferably 2.

$R^1$ is preferably $CF_3$, aryl or arylalkyl, or an alkyl, alkenyl, cycloalkyl or cycloalkylalkyl group, optionally substituted as described previously. Preferred substituents include halogen (especially fluorine or chlorine), $CF_3$, CN, $OR^3$ (especially OH, OMe and OEt), $COR^3$ (especially acetyl), $CO_2R^3$ (especially $CO_2H$, $CO_2Me$ and $CO_2Et$), $SO_2R^4$ (especially methanesulfonyl), $N(R^5)_2$ (especially when the $R^5$ groups complete a ring) and $CON(R^5)_2$ (especially $CONH_2$).

Examples of alkyl groups represented by $R^1$ include methyl, ethyl, n-propyl, isopropyl, n-butyl, t-butyl, isobutyl, 2,2,2-trifluoroethyl, chloromethyl, 3-chloropropyl, 2-chloro-2-propyl, cyanomethyl, 2-hydroxyethyl, 2-methoxyethyl, 2-hydroxy-2-methylpropyl, carboxymethyl, methoxycarbonylmethyl, 1-carboxyethyl, 1-ethoxycarbonylethyl, carbamoylmethyl, 2-(pyrrolidin-1-yl)ethyl, 2-(morpholin-4-yl)ethyl and $MeSO_2CH_2$—.

Examples of alkenyl groups represented by $R^1$ include vinyl and allyl.

Examples of cycloalkyl and cycloalkylalkyl groups represented by $R^1$ include cyclopropyl, cyclobutyl, cyclopentyl, cyclohexyl, cyclopropylmethyl and cyclopentylmethyl.

When $R^1$ represents aryl or arylalkyl, the aryl group may be phenyl or heteroaryl (especially 5- or 6-membered heteroaryl), optionally substituted as defined previously. Preferred substituents include halogen (especially chlorine, bromine or fluorine), CN, $CF_3$, $OCF_3$, alkyl (especially methyl), OH, alkoxy (especially methoxy) and alkoxycarbonyl (such as methoxycarbonyl). Preferred heteroaryl groups include pyridine, pyrimidine, furan, thiophene, thiazole, isothiazole, isoxazole, pyrazole, imidazole, triazole, thiadiazole and tetrazole, especially pyridine, furan, thiophene, thiazole, isothiazole, isoxazole, pyrazole, imidazole, triazole, and tetrazole.

Examples of aryl groups represented by $R^1$ include phenyl, 2-, 3- and 4-fluorophenyl, 2,4-difluorophenyl, 2-chlorophenyl, 2-bromophenyl, 2-cyanophenyl, 2-methylphenyl, 2-trifluoromethylphenyl, 2-methoxyphenyl, 5-chloro-2-methoxyphenyl, 2-pyridyl, 4-pyridyl, 6-chloro-3-pyridyl, 2-furyl, 2-thienyl, 3-thienyl, 2-thiazolyl, 5-isothiazolyl, 2-imidazolyl, 2-methylfuran-3-yl, 5-chloro-2-thienyl, 4-chloro-2-thienyl, 3-chloro-2-thienyl, 3-bromo-2-thienyl, 4-bromo-2-thienyl, 5-methyl-2-thienyl, 2-(methoxycarbonyl)-3-thienyl, 4-methylthiazol-3-yl, 1-methylimidazol-2-yl, 1-methylimidazol-5-yl, 1-methylimidazol-4-yl, 3-chloro-1,5-dimethylpyrazol-4-yl, 3,5-dimethylisoxazol-4-yl, 1-methyl-1,2,3,4-tetrazol-5-yl, 1,2,4-triazol-3-yl, 1-methyl-1,2,4-triazol-3-yl, 2-methyl-1,2,4-triazol-3-yl and 4-methyl-1,2,4-triazol-3-yl.

Arylalkyl groups represented by $R^1$ are typically optionally substituted benzyl, phenethyl, heteroarylmethyl or heteroarylethyl groups. Examples include benzyl, 2-furylmethyl, 2-thienylmethyl and 1-(2-thienyl)ethyl. Preferred examples include benzyl.

$R^2$ preferably represents H or methyl, most preferably H.

$R^3$ preferably represents H, $C_{1-4}$alkyl, phenyl, pyridyl, or 5-membered heteroaryl. Most preferably, $R^3$ represents H or $C_{1-4}$alkyl.

$R^4$ preferably represents $C_{1-4}$alkyl, phenyl, pyridyl, or 5-membered heteroaryl. Most preferably, $R^3$ represents $C_{1-4}$alkyl.

$Ar^1$ and $Ar^2$ independently represent optionally substituted phenyl or heteroaryl. $Ar^1$ is preferably selected from optionally substituted phenyl and optionally substituted 6-membered heteroaryl. Preferred 6-membered heteroaryl embodiments of $Ar^1$ include optionally substituted pyridyl, in particular optionally substituted 3-pyridyl. $Ar^1$ is preferably selected from 6-(trifluoromethyl)-3-pyridyl and phenyl which is optionally substituted in the 4-position with halogen, CN, vinyl, allyl, acetyl, methyl or mono-, di- or trifluoromethyl. In one preferred embodiment of the invention $Ar^1$ represents 4-chlorophenyl. In another preferred embodiment $Ar^1$ represents 4-trifluoromethylphenyl. In a further preferred embodiment, $Ar^1$ represents 6-(trifluoromethyl)-3-pyridyl.

$Ar^2$ preferably represents optionally substituted phenyl, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5-positions or in the 2-, 3- and 6-positions, or from phenyl groups bearing a fluorine substituent in the 2-position and halogen, CN, methyl or hydroxymethyl in the 5-position. In a preferred embodiment of the invention, $Ar^2$ represents 2,5-difluorophenyl.

In a particular embodiment, $Ar^1$ is 6-trifluoromethyl-3-pyridyl, 4-chlorophenyl or 4-trifluoromethylphenyl and $Ar^2$ is 2,5-difluorophenyl.

A preferred subclass of the compounds of the invention are the compounds of formula II:

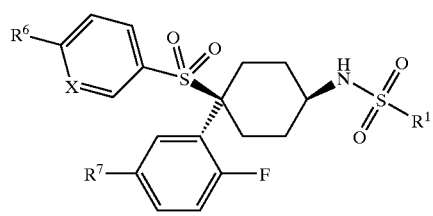

II wherein X represents N or CH;
$R^6$ represents H, F, Cl, Br, CN, $CF_3$, $CH=CH_2$ or $CH_3$;
$R^7$ represents F, Cl, Br, CN, $CH_3$ or $CH_2OH$; and
$R^1$ has the same definition and preferred identities as before;
and pharmaceutically acceptable salts thereof.
When X represents N, $R^6$ is preferably $CF_3$.
In a preferred embodiment, $R^1$ is selected from:
(a) $CF_3$;
(b) $C_{1-6}$alkyl which optionally bears up to 2 substituents selected from halogen, CN, $CF_3$, $OR^3$, $CO_2R^3$, $SO_2R^4$, $N(R^5)_2$, and $CON(R^5)_2$; and
(c) phenyl, pyridyl or 5-membered heteroaryl which optionally bear up to 3 substituents selected from halogen, CN, $CF_3$, $OR^3$, $COR^3$, $CO_2R^3$, $OCOR^4$, $N(R^5)_2$, $CON(R^5)_2$ and optionally-substituted $C_{1-6}$alkyl, $C_{1-6}$alkoxy, $C_{2-6}$alkenyl or $C_{2-6}$alkenyloxy wherein the substituent is selected from halogen, CN, $CF_3$, phenyl, $OR^3$, $CO_2R^3$, $OCOR^4$, $N(R^5)_2$ and $CON(R^5)_2$;
where $R^3$, $R^4$ and $R^5$ have the same definitions and preferred identities as before.
$R^1$ very aptly represents $CF_3$.

Examples of individual compounds in accordance with the invention are provided in the Examples section appended hereto.

The compounds of formula I have an activity as modulators of the processing of APP by γ-secretase.

The invention also provides pharmaceutical compositions comprising one or more compounds of formula I or the pharmaceutically acceptable salts thereof and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 250 mg, for example 1, 2, 5, 10, 25, 50, 100, 200 or 250 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

The present invention further provides a method of treatment of a subject suffering from or prone to a condition associated with the deposition of β-amyloid which comprises administering to that subject an effective amount of a compound according to formula I or a pharmaceutically acceptable salt thereof. Preferably the condition is a neurological disease having associated β-amyloid deposition such as Alzheimer's disease.

For treating or preventing Alzheimer's Disease, a suitable dosage level is about 0.01 to 250 mg/Kg per day, preferably about 0.10 to 100 mg/Kg per day, especially about 1.0 to 50 mg/Kg, and for example about 10 to 30 mg/Kg of body weight per day. Thus, a dose of about 500 mg per person per day may be considered. The compounds may be administered on a regimen of 1 to 4 times per day. In some cases, however, dosage outside these limits may be used.

The compounds of formula I in which $R^2$ is H may be prepared by reacting a sulfinyl chloride $R^1SOCl$ or a sulfo nyl chloride $R^1SO_2Cl$ or a sulfonic anhydride $(R^1SO_2)_2O$ with an amine of formula III:

III

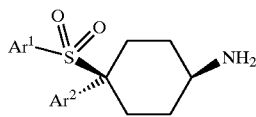

where $R^1$, $Ar^1$ and $Ar^2$ have the same meanings as before. The reaction is typically carried out at ambient or reduced temperature in the presence of a tertiary amine such as triethylamine in an aprotic solvent such as dichloromethane.

The compounds of formula I in which $R^2$ is other than H may be prepared by alkylation of the corresponding compounds of formula I in which $R^1$ is H, e.g. by heating with the appropriate alkyl iodide in THF in the presence of sodium hydride.

The amines of formula III may be obtained by reduction of the azides IV:

IV

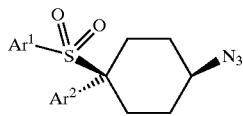

where $Ar^1$ and $Ar^2$ have the same meanings as before. The azides IV are obtained via nucleophilic displacement of the mesylates V(a), formed from the trans alcohols V(b) by reaction with methanesulfonyl chloride:

V

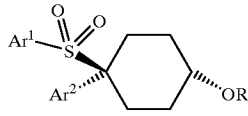

(a) $R=SO_2Me$
(b) $R=H$ where $Ar^1$ and $Ar^2$ have the same meanings as before. The alcohols V(b) are obtained by reduction of the cyclohexanones VI:

VI

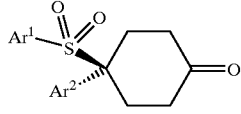

where $Ar^1$ and $Ar^2$ have the same meanings as before. The reduction may be carried out using sodium borohydride in ethanol, with isolation of the trans isomer by chromatography.

The synthesis of cyclohexanones VI and their conversion to amines III, is described in WO 02/081435.

It will be apparent to those skilled in the art that individual compounds of formula I prepared by the above routes may be converted into other compounds in accordance with formula I by means of well known synthetic techniques such as alkylation, esterification, amide coupling, hydrolysis, oxidation and reduction. Such techniques may likewise be carried out on precursors of the compounds of formula I. For example, substituents on the aromatic groups $Ar^1$ or $Ar^2$ may be added or interconverted by means of standard synthetic processes carried out on the compounds of formula I or their precursors. For example, a chlorine or bromine atom on $Ar^1$ or $Ar^2$ may be replaced by vinyl by treatment with vinyltributyltin in the presence of tri-t-butylphosphine, cesium fluoride and tris(dibenzylideneacetone)dipalladium(0). Ozonolysis of the vinyl group provides the corresponding formyl derivative, which may be transformed in a variety of ways, including oxidation to the corresponding acid, reduction to the corresponding benzyl alcohol, and conversion to the corresponding nitrile by treatment with hydroxylamine then triphenylphosphine and carbon tetrachloride.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

An assay which can be used to determine the level of activity of compounds of the present invention is described in WO01/70677. A preferred assay to determine such activity is as follows:

1) SH-SY5Y cells stably overexpressing the βAPP C-terminal fragment SPA4CT, are cultured at 50–70% confluency. 10 mM sodium butyrate is added 4 hours prior to plating.
2) Cells are plated in 96-well plates at 35,000 cells/well/100 μL in Dulbecco's minimal essential medium (DMEM) (phenol red-free)+10% foetal bovine serum (FBS), 50 mM HEPES buffer (pH7.3), 1% glutamine.
3) Make dilutions of the compound plate. Dilute stock solution 18.2× to 5.5% DMSO and 11× final compound concentration. Mix compounds vigorously and store at 4° C. until use.
4) Add 10 μL compound/well, gently mix and leave for 18 h at 37° C., 5% $CO_2$.
5) Prepare reagents necessary to determine amyloid peptide levels, for example by Homogeneous Time Resolved Fluorescence (HTRF) assay.

6) Plate 160 μL aliquots of HTRF reagent mixture to each well of a black 96-well HTRF plate.
7) Transfer 40 μL conditioned supernatant from cell plate to HTRF plate. Mix and store at 4° C. for 18 hours.
8) To determine if compounds are cytotoxic following compound administration, cell viability is assessed by the use of redox dye reduction. A typical example is a combination of redox dye MTS (Promega) and the electron coupling reagent PES. This mixture is made up according to the manufacturer's instructions and left at room temperature.
9) Add 10 μL/well MTS/PES solution to the cells; mix and leave at 37° C.
10) Read plate when the absorbance values are approximately 0.4–0.8. (Mix briefly before reading to disperse the reduced formazan product).
11) Quantitate amyloid beta 40 peptide using an HTRF plate reader. Alternative assays are described in *Biochemistry*, 2000, 39(30), 8698–8704. See also, *J. Neuroscience Methods*, 2000, 102, 61–68.

The Examples of the present invention all had an $ED_{50}$ of less than 0.5 μM, in most cases less than 100 nM, and in preferred cases less than 10 nM, in at least one of the above assays.

The following examples illustrate the present invention.

EXAMPLES

Intermediate A 4-(4-chlorobenzenesulfonyl)-4-(2,5-difluorophenyl) cyclohexylamine

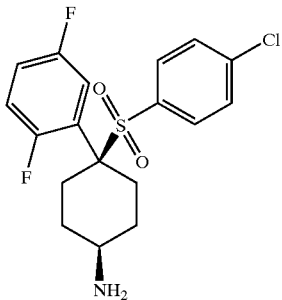

(1) 4-Chlorothiophenol (3.6 g, 0.025 mol) in dichloromethane (100 mL) was treated with 2,5-difluorobenzyl bromide (5.17 g, 0.025 mol) and triethylamine (3.9 ml, 0.028 mol). The reaction was stirred for 2 hours then diluted with dichloromethane (250 mL) and washed with water (100 mL) and brine (100 mL). The separated organic layer was dried ($MgSO_4$), evaporated to dryness, and the product purified by passing down a plug of silica eluting with hexane-ethyl acetate mixtures to give 4-chlorophenyl 2,5-difluorobenzyl sulfide (5.12 g). $^1H$ NMR $CDCl_3$ 7.23 (4H, s), 6.69–6.86 (3H, m) and 4.04 (2H, s).

(2) This thioether (5.12 g, 0.018 mol) in dichloromethane (100 mL) was treated with m-chloroperoxybenzoic acid (50% w/w, 14.3 g, 0.042 mol) and stirred for 2 hours. The reaction was washed with sodium sulfite (5% aqueous, 100 mL) and brine (50 mL), dried ($MgSO_4$) and evaporated to dryness. The sulfone product was purified by flash chromatography on silica eluting with hexane-ethyl acetate mixtures to give the sulfone (3.6 g). $^1H$ NMR ($CDCl_3$) δ 7.61 (2H, d, J=8.6 Hz), 7.45 (2H, d, J=8.6 Hz), 7.13–7.08 (1H, m), 7.05–7.01 (1H, m), 6.99–6.87 (1H, m) and 4.36 (2H, s).

(3) A solution of this sulfone (1 g, 3.31 mmol) and methyl acrylate (0.84 mL, 9.27 mmol) in tetrahydrofuran (30 mL) was treated dropwise with potassium ⁱbutoxide (1M solution in tetrahydrofuran, 3.64 mL, 3.64 mmol). The reaction was stirred for 2 hours, diluted with ethyl acetate (100 mL) and washed with water (50 mL) and brine (50 mL). The organic phase was separated, dried ($MgSO_4$) and evaporated to dryness, and the product purified by flash chromatography on silica eluting with hexane-ethyl acetate mixtures to give 1.0 g 4,4-disubstituted-2-hydroxycyclohexene-1-carboxylate product. $^1H$ NMR ($CDCl_3$) δ 12.0 (1H, s), 7.41 (4H, s), 7.06–7.0 (2H, m), 6.87–6.81 (1H, s), 3.81 (3H, s), 3.38 (1H, dd, J=3.2, 15.8 Hz), 3.02–2.92 (2H, m), 2.52 (1H, dd, J=5.7, 18.5 Hz), 2.3–2.2 (1H, m) and 2.2–2.1 (1H, m).

(4) The ester from the foregoing step (1.0 g, 2.25 mmol) in dimethylsulfoxide (10 mL) was treated with sodium chloride (0.3 g, 4.96 mmol) and water (0.9 mL, 4.96 mmol) and heated at 150° C. for 2 hours. The cooled reaction mixture was diluted with ethyl acetate (100 mL), washed with saturated aqueous ammonium chloride solution (100 mL), dried ($MgSO_4$) and evaporated to dryness. The product was purified by flash chromatography on silica eluting with hexane-ethyl acetate mixtures to give 4-[(4-chlorophenyl)sulfonyl]-4-(2,5-difluorophenyl) cyclohexanone (0.5 g). $^1H$ NMR ($CDCl_3$) δ 7.43–7.37 (4H, m), 7.22–7.1 (2H, m), 6.97–6.9 (1H, m), 3.05–2.98 (2H, m), 2.61–2.53 (4H, m) and 2.25–2.15 (2H, m).

(5) The cyclohexanone (0.1 g, 0.26 mmol) in methanol (2 ml) was treated with $NaBH_4$ (0.098 g, 0.26 mmol), stirred for 1 hour, quenched with HCl (1N, 10 ml), diluted with ethyl acetate (20 ml), then the organic phase was separated, dried ($MgSO_4$) and evaporated to dryness. The trans 4-[(4-chlorophenyl)sulfonyl]-4-(2,5-difluorophenyl)cyclohexanol was purified on silica eluting with hexane-ethyl acetate mixtures. 0.052 g. $^1H$ NMR $CDCl_3$ 7.39–7.33 (4H, m), 7.11–7.02 (2H, m), 6.88–6.82 (1H, m), 3.80–3.73 (1H, m), 2.80–2.60 (2H, m), 2.22–2.16 (2H, m), 2.08–2.04 (2H, m), 1.53(1H, br) and 1.27–1.13 (2H, m).

(6) To this alcohol (2.7 g, 6.9 mmol) and triethylamine (1.45 ml, 10.3 mmol) in dichloromethane (50 ml) was added methanesulfonyl chloride (0.645 ml, 8.9 mmol) at −30° C. After 30 minutes the mixture was washed with water (20 ml), 10% aqueous citric acid (20 ml) and saturated aqueous sodium hydrogen carbonate (50 ml), dried ($MgSO_4$) and evaporated to dryness. The solid was triturated with ether to give the mesylate (2.6 g) $^1H$ NMR ($CDCl_3$) 7.40–7.37 (4H, m), 7.12–7.07 (2H, m), 6.92–6.83 (1H, m), 4.78–4.65 (1H, m), 2.96 (3H, s), 2.88–2.52 (2H, m), 2.29–2.21 (4H, m) and 1.59–1.47 (2H, m).

(7) The mesylate (1.5 g, 3.2 mmol) in dimethylformamide (5 ml) was treated with sodium azide (315 mg, 4.8 mmol) and heated to 90° C. for 6 hrs. The mixture was treated with water (80 ml), and extracted with diethyl ether (3×50 ml), dried ($MgSO_4$) and evaporated to dryness. The solid was triturated with ether to give the cis azide (1.4 g) $^1H$ NMR ($CDCl_3$) 7.40–7.34 (4H, m), 7.12–7.03 (2H, m), 6.90–6.83 (1H m), 3.78–3.76 (1H, m), 2.62–2.41 (4H, m), 1.97–1.91 (2H, m) and 1.51–1.41 (2H, m).

(8) The azide (1 g, 2.55 mmol) in tetrahydrofuran (10 ml) and water (1 ml), was treated with triphenylphosphine (740 mg, 2.8 mmol) at room temperature for 15 mins, water (5 ml) was added and the mixture was heated at reflux for 4 hrs. After cooling to room temperature and passage through SCX Varian Bond Elut™ cartridge, the basic fraction was evaporated to give the primary amine. 1H NMR ($CDCl_3$) 7.35 (4H, s), 7.12–7.01 (2H, m), 6.88–6.81 (1H, m), 3.13–3.11 (1H, m) 2.64–2.44 (4H, m), 1.78–1.68 (2H, m) and 1.52–1.39 (2H, m). MS MH+ 386(388).

Intermediate B 4-(2,5-difluorophenyl)-4-(4-trifluoromethylbenzenesulfonyl)cyclohexylamine

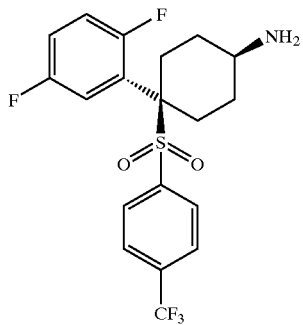

Prepared as for Intermediate A, using 4-(trifluoromethyl) thiophenol in step (1), except that the borohydride reduction of step (5) was carried out at −20° C. MS (ES+) MH+ 420

Intermediate C 4-(2,5-difluorophenyl)-4-(6-trifluoromethyl-pyridine-3-sulfonyl)-cyclohexylamine

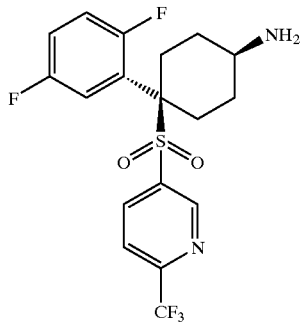

(1) A solution of 3-amino-6-(trifluoromethyl)pyridine (1.62 g, 0.01 mol) in concentrated hydrochloric acid (1.7 mL), was treated with ice (2 g) and cooled to 0° C. Sodium nitrite (0.71 g, 0.01 mol) in water (2 mL) was added slowly, the reaction mixture stirred for 5 minutes at 0° C. then treated slowly with a solution of potassium ethyl xanthate (1.92 g, 0.012 mol) in ethanol-water. The reaction mixture was heated at 50–55° C. for 30 minutes, cooled and diluted with diethyl ether and water. The organic layer was washed with brine, dried (MgSO$_4$) and evaporated in vacuo. The resulting xanthate was dissolved in ethanol (30 mL) and treated with potassium hydroxide (3 g) and refluxed (90° C.) for 2 h. After cooling and filtering, the filtrate was acidified with citric acid and diluted with diethyl ether. The organic layer was washed with brine, dried (MgSO$_4$) and evaporated in vacuo. Purification by column chromatography on silica gave the (trifluoromethyl)pyridinethiol as a yellow oil (0.79 g, 44%).

$^1$H NMR (360 MHz, CDCl$_3$) δ 8.57 (1H, d, J=2.0 Hz), 7.74 (1H, dd, J=8.1, 2.0 Hz), 7.54 (1H, d, J=8.1 Hz), 3.62 (1H, s).

(2) This thiol (0.5 g, 2.8 mmol) was reacted first with 2,5-difluorobenzyl bromide and subsequently with 3-chloroperoxybenzoic acid by the procedure described for Intermediate A to gave the pyridyl benzyl sulfone as a white powder (0.82 g, 87% over 2 steps).

$^1$H NMR (400 MHz, CDCl$_3$) δ 8.93 (1H, d, J=2.1 Hz), 8.18 (1H, dd, J=8.1, 2.1 Hz), 7.80 (1H, d, J=8.1 Hz), 7.21–7.17 (1H, m), 7.10–7.04 (1H, m), 6.93–6.88 (1H, m), 4.46 (2H, s).

(3) This sulfone (50 mg, 0.15 mmol) in tetrahydrofuran (5 mL) at 0° C. was treated with potassium tert-butoxide (17 mg, 0.15 mmol), then with 2,2-bis(2-iodoethyl)-1,3-dioxolane (H. Niwa et al, J. Am. Chem. Soc., 1990, 112, 9001) (86 mg, 0.23 mmol), stirred for 1 h at room temperature and then for 1 h at 70° C. The cooled reaction mixture was treated with more potassium tert-butoxide (1.2 equivalents) and 2,2-bis(2-iodoethyl)-1,3-dioxolane (0.3 equivalents). After heating at 70° C. for 1 h, then cooling to room temperature, the reaction mixture was diluted with diethyl ether and water, the layers separated and the organic layer washed with water and brine, dried (MgSO$_4$) and evaporated in vacuo. Purification by column chromatography on silica gave the desired cyclohexanone cyclic ketal (38 mg, 56%) as a white solid.

$^1$H NMR (360 MHz, CDCl$_3$) δ 8.68 (1H, d, J=2.0 Hz), 7.92 (1H, dd, J=2.0, 8.1 Hz), 7.73 (1H, d, J=8.1 Hz), 7.19–7.07 (2H, m), 6.90–6.82 (1H, m), 3.99–3.88 (4H, m), 2.7 (2H, vbrm), 2.5 (2H, vbrappt), 1.85 (2H, brappd), 1.54–1.26 (2H, m).

(4) This ketal (30 mg, 0.065 mmol) was heated at 50° C. overnight with p-toluenesulfonic acid (15 mg) in 80% acetic acid-water. The reaction mixture was partitioned between diethyl ether and water and the organic layer washed with saturated aqueous sodium hydrogencarbonate solution and brine, dried (MgSO$_4$) and evaporated in vacuo. Purification by column chromatography on silica gave the cyclohexanone (25 mg, 92%) as a white solid.

$^1$H NMR (400 MHz, CDCl$_3$) δ 8.67 (1H, d, J=2.0 Hz), 7.97 (1H, dd, J=8.1, 2.0 Hz), 7.77 (1H, d, J=8.1 Hz), 7.28–7.16 (2H, m), 6.99–6.90 (1H, m), 3.01–2.97 (2H, m), 2.68–2.57 (4H, m), 2.26–2.17 (2H, m).

(5) The cyclohexanone was converted to the title amine by the procedure of Intermediate A, except that the borohydride reduction was carried out at −78° C. M/Z 421 (MH$^+$).

Sulfonyl Chlorides

The sulfonyl chlorides used in these examples were typically commercially available, or available by literature routes. Representative syntheses include the following:

2-methyl-1-propanesulfonyl chloride

To 2-methyl-1-propanethiol (200 mg, 2.22 mmol) at 0° C. in acetonitrile under nitrogen was added KNO$_3$ (561 mg, 5.5 mmol) then sulfuryl chloride (0.45 ml, 5.5 mmol). The reaction mixture was stirred at 0° C. for 3 h, diluted with NaHCO$_3$ and extracted with ethyl acetate. The combined organic layers were washed with brine, dried (MgSO$_4$) and evaporated to give the sulfonyl chloride (293 mg, 95%) $^1$H NMR (CDCl$_3$) 3.65–3.63 (2H, d, J=6.5 Hz), 2.55–2.49 (1H, m), 1.19–1.18 (6H, d, J=6.7 Hz)

2-chlorosulfonyl-1-methylimidazole

Bleach (12% w/w aq, 110 ml) was cautiously added dropwise to a solution of 2-mercapto-1-methylimidazole (2.0 g) in conc. H$_2$SO$_4$ (50 ml) cooled to 0° C. After stirring 30 minutes at 0° C. the mixture was diluted with H$_2$O (30 ml) and dichloromethane (30 ml). The aqueous layer was re-extracted with dichloromethane and the combined organic layers dried (MgSO$_4$) and evaporated to give the product as an oil (730 mg).

5-chlorosulfonyl-1-methyltetrazole

Cl$_2$(g) was bubbled through a solution of 5-mercapto-1-methyltetrazole (1.518 g) in 2N HCl (25 ml) at 0° C. After 15 minutes the solid precipitate (880 mg) was filtered off and washed with H$_2$O.

Example 1 methanesulfonic acid, N-[4-(4-chlorobenzenesulfonyl)-4-(2,5-difluorophenyl)-cyclohexyl]-amide

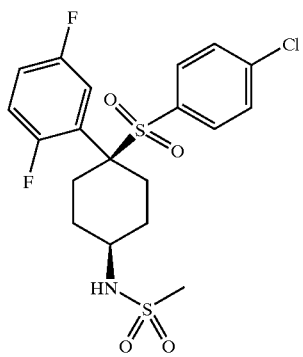

Methanesulfonyl chloride (24 μL, 0.31 mmol) was added to a solution of Intermediate A (100 mg, 0.28 mmol) and triethylamine (77 μL, 0.56 mmol) in dichloromethane (1.5 ml) at 0° C. After stirring at ambient temperature for 12 hours, the reaction was partitioned between water (50 ml) and dichloromethane (50 ml), the phases separated and the aqueous layer washed twice more with dichloromethane. The combined organic layers were washed with 1N HCl. the acidic layer extracted twice with dichloromethane and the combined organics dried over $K_2CO_3$ and concentrated. Flash column chromatography eluting with 60/40 hexane/ethyl acetate afforded the title compound (88.5 mg).

$^1$H NMR CDCl$_3$ 7.34 (4H, m), 7.06 (2H, m), 6.85 (1H, m), 4.72 (1H, d, J=6.67 Hz), 3.65 (1H, m), 3.00 (3H, s), 2.58 (2H, m), 2.42 (2H, t, J=13.68 Hz), 2.00 (2H, m), 1.60 (1H, m), 1.53 (1H, m). MS(ES$^-$) [M−H] 462, 464.

The following examples were prepared by the same procedure:

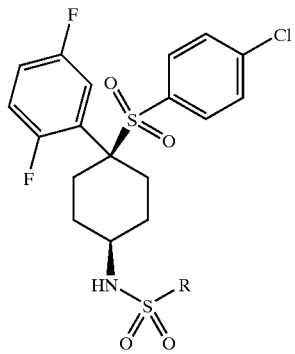

| Example | R | MS (ES$^-$ (MH$^-$) unless otherwise stated) |
|---|---|---|
| 2 | CH$_2$CF$_3$ | 530, 532 |
| 3 | $^n$Pr | 490, 492 |
| 4 | benzyl | 538, 540 |
| 5 | phenyl | 524, 526 |
| 6 | 2-thienyl | 530, 532 |
| 7 | ethyl | 476, 478 |
| 8 | 5-chloro-2-thienyl | 566, 568 (M + H)$^+$ |
| 9 | n-butyl | 504, 506 |
| 10 | 2-fluorophenyl | 542, 544 |
| 11 | 3-fluorophenyl | 542, 544 |
| 12 | 4-fluorophenyl | 542, 544 |

-continued

| Example | R | MS (ES$^-$ (MH$^-$) unless otherwise stated) |
|---|---|---|
| 13 | 2-pyridyl | 525, 527 |
| 14 | 5-methyl-2-thienyl | 546, 548 (MH)$^+$ |
| 15 | 5-isothiazolyl | 531, 533 |
| 16 | 4-chloro-2-thienyl | 564, 566, 568 |
| 17 | 2-(trifluoromethyl)phenyl | 616/618[M + Na]$^+$. |
| 18 | CH$_2$CH(CH$_3$)$_2$ | 506, 508[MH]$^+$ |
| 19 | CH$_2$SO$_2$Me | 542, 544[MH]$^+$ |
| 20 | 2-methylphenyl | 540, 542[MH]$^+$ |
| 21 | 1-methyl-5-methyl-1,2,4-triazol-3-yl | 529, 531 |
| 22 | 2-thiazolyl | 531, 533 |
| 23 | chloromethyl | 494, 496, 498 |
| 24 | 2-furyl | 514, 516 |
| 25 | 2-chlorophenyl | 558, 560 |
| 26 | 2-cyanophenyl | 549, 551 |
| 27 | 3,4,5-trimethylisoxazol-yl | 543, 545 |
| 28 | 3-thienyl | 530, 532 |
| 29 | 3-chloropropyl | 524, 526 |
| 30 | 1,5-dimethyltetrazol-yl | 532, 543[MH]$^+$ |
| 31 | 5-methyl-1H-1,2,4-triazol-3-yl | 517, 519[MH]$^+$ |
| 32 | 3-chloro-2-thienyl | 564, 566 |
| 33 | 1-methylimidazol-yl | 530, 532[MH]$^+$ |

-continued

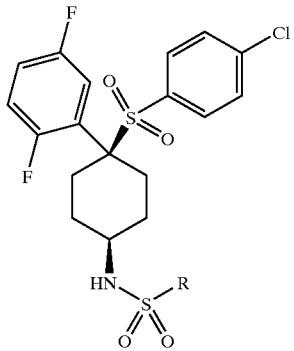

| Example | R | MS (ES⁻ (MH⁻) unless otherwise stated) |
|---|---|---|
| 34 | Me-imidazolyl | 530, 532[MH]⁺ |
| 35 | N-methylimidazolyl | 528, 530 |
| 36 | 2-bromophenyl | 430 [MH-4-Cl-PhSO₂]⁺ |
| 37 | dimethyl-chloro-pyrazolinyl | * |

* ¹H NMR (DMSO) 7.93(1H, d, J=3.9Hz), 7.64–7.62(2H, d, J=8.6Hz), 7.37–7.27(3H, m), 7.21–7.09(2H, m), 3.75(3H, s), 3.15(1H, d, J=2.0Hz), 2.43–2.44(2H, m), 2.32(2H, dd, J=12.1 and 0.8Hz), 2.28(3H, s), 1.77(2H, dd, J=13.3 and 1.2Hz), 1.29–1.22(2H, m)

Example 38
{N-[4-(4-chlorobenzenesulfonyl)-4-(2,5-difluorophenyl)-cyclohexyl]-aminosulfonyl}acetic acid, methyl ester

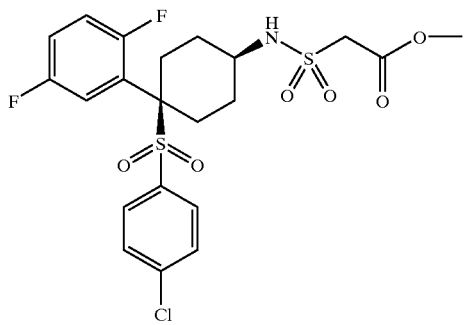

To a stirred solution of chlorosulfonyl acetyl chloride (1 g of 95% purity, 5.7 mmol) in tetrahydrofuran (20 ml) under nitrogen was added methanol (0.23 ml, 5.7 mmol). The reaction mixture was stirred at ambient temperature over 2 h. After this time, the reaction was evaporated to afford the chlorosulfonyl methyl ester which was coupled to Intermediate A (100 mg, 0.28 mmol) by the procedure of Example 1 to afford the desired product. ¹H NMR (CDCl₃) 7.39–7.32 (4H, m), 7.08–7.04 (2H, m), 6.89–6.82 (1H, m), 5.38 (1H, d, J=5.6 Hz), 4.03 (2H, s), 3.84 (3H, s), 3.64–3.59 (1H, m), 2.62–2.24 (2H, m), 2.49–2.42 (2H, m), 2.08–2.04 (2H, m), 1.59–1.49 (2H, m); m/z(ES⁻)=520/522

Example 39
methanesulfinic acid, N-[4-(4-chlorobenzenesulfonyl)-4-(2,5-difluorophenyl)-cyclohexyl]-amide

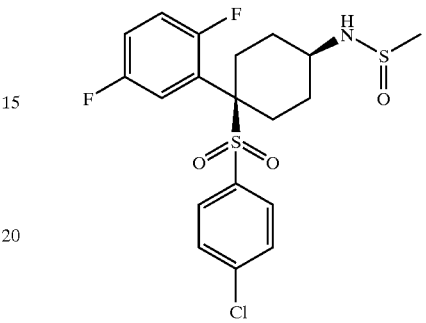

Prepared by the procedure of Example 1 using methyl sulfinyl chloride (prepared from dimethyldisulfide following the procedure described in Corey et. al *J. American Chem. Soc.*, 1968, 90(20), 5548–5552). m/z (ES⁺)=272[M−ArSO₂⁻]⁺, m/z=448[MH]⁺ and m/z=470[M+Na]⁺

Example 40
3-bromothiophene-2-sulfonic acid, N-[4-(4-chlorobenzenesulfonyl)-4-(2,5-difluorophenyl)-cyclohexyl]-amide

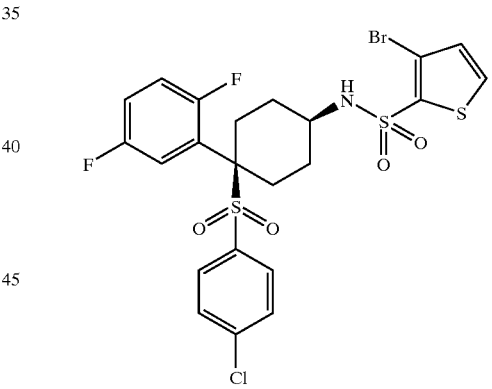

3-Bromothiophene (16.1 g, 98.8 mmol) at −78° C. in dichloromethane (40 ml) under nitrogen was treated dropwise with chlorosulfonic acid (40 ml, 602 mmol) over 1 h. The reaction mixture was stirred for 3 h at ambient temperature, then cautiously poured onto ice (1500 ml) and extracted with dichloromethane (3×150 ml). The combined organic layers were washed with brine, dried (MgSO₄) and evaporated to give a residue (18 g) which was purified using preparative thin layer chromatography eluting with 3% ethyl acetate:hexane to afford 4-bromo-2-thiohenesulfonylchloride (320 mg) as the minor product, and 3-bromo-2-chlorothiophenesulfonyl chloride as the major product (4.5 g). The 3-bromo-isomer was coupled to Intermediate A by the procedure of Example 1.

¹H NMR (CDCl₃) 7.50–7.48 (2H, dd, J=8.8 and 1.5 Hz), 7.39–7.31 (4H, m), 7.07–7.02 (2H, m), 6.87–6.80 (1H, m), 5.14–5.12 (1H, d, J=6.5 Hz), 3.53–3.49 (1H, m), 2.53–2.56

(2H, m), 2.41–2.34 (2H, t, J=13.6 Hz), 1.90–1.86 (2H, m), 1.68–1.45 (2H, m) and m/z(ES–)=610, 612

Example 41

4-bromothiophene-2-sulfonic acid, N-[4-(4-chlorobenzenesulfonyl)-4-(2,5-difluorophenyl)-cyclohexyl]-amide

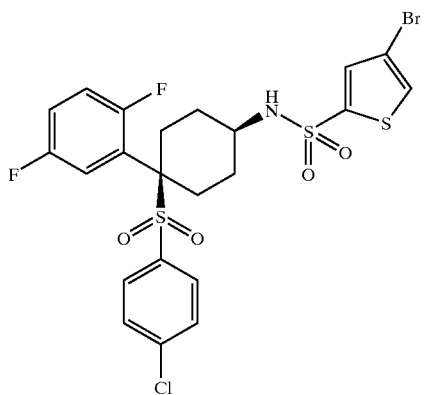

Prepared as for Example 40, using the 4-bromo-2-thiophenesulfonyl chloride.

¹H NMR (CDCl₃) 7.50–7.49 (1H, d, J=5.2 Hz), 7.41–7.32 (4H, m), 7.13–7.12 (1H, d, J=5.2 Hz), 7.06–7.01 (2H, m), 6.83–6.79 (1H, m), 5.42–5.40 (1H, d, J=6.6 Hz), 3.49–3.45 (1H, m), 2.57–2.54 (2H, m), 2.44–2.37 (2H, m), 1.91–1.87 (2H, m), 1.59–1.41 (2H, m) and m/z(ES–)=610, 612

Example 42

2-methoxy-5-chlorobenzenesulfonic acid, N-[4-(4-chlorobenzenesulfonyl)-4-(2,5-difluorophenyl)-cyclohexyl]-amide

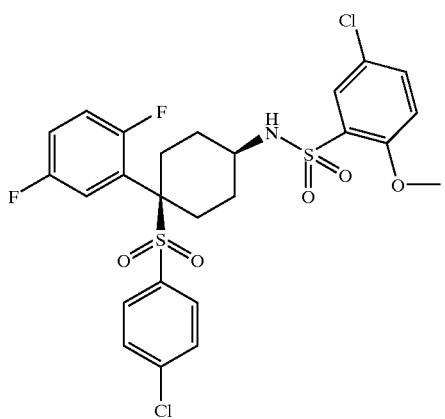

To a solution of 2-methoxybenzenethiol (200 mg, 1.43 mmol) in acetonitrile under nitrogen at 0° C. was added KNO₃ (361 mg, 3.6 mmol) then sulfuryl chloride.(0.29 ml, 3.6 mmol). The reaction mixture was stirred at 0° C. for 5 h, then diluted with NaHCO₃ and extracted with ethyl acetate. The combined organic layers were washed with brine, dried (MgSO₄) and evaporated to give a residue (264 mg) which was coupled in the same manner as in Example 1 to afford a 1:1 mixture (80 mg) which was purified using preparative thin layer chromatography eluting with ethyl acetate:dichloromethane:hexane 1:1:2 to give the 2-methoxy-5-chlorophenylsulfonyl derivative (40 mg).

M/z(ES–)=588/590

Example 43

2-methoxybenzenesulfonic acid, N-[4-(4-chlorobenzenesulfonyl)-4-(2,5-difluorophenyl)-cyclohexyl]-amide

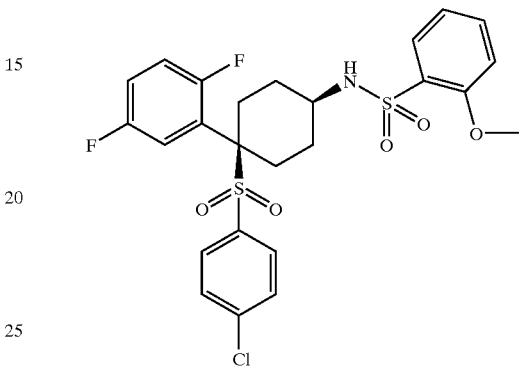

Isolated from the product mixture of Example 42 using preparative thin layer chromatography eluting with ethyl acetate:dichloromethane:hexane 1:1:2.

Yield 20 mg. M/z(ES–)=554/556

Example 44

[4-(4-Chlorobenzenesulfonyl)-4-(2,5-difluorophenyl)cyclohexyl]aminosulfonyl-acetamide

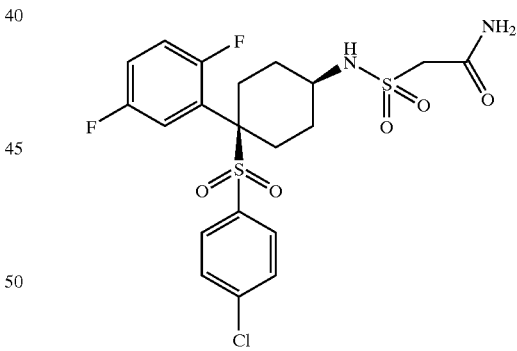

The ester of Example 38 (40 mg, 0.07 mmol) in ethanol (1.5 ml) was treated with NH₃ (1 ml of 25% aqueous solution). The reaction mixture was stirred at ambient temperature for 2 h and evaporated to give a residue (40 mg) which was purified using preparative plate thin layer chromatography eluting with ethyl acetate:hexane 2:1 to yield the desired product (10 mg).

¹H NMR (CDCl₃) 7.38–7.31(4H, m), 7.08–7.03 (2H, m), 6.89–6.83 (1H, m), 6.54 (1H, s), 6.06 (1H, s), 5.78 (1H, d, J=6.1 Hz), 3.97 (1H, s), 3.65–3.63 (1H, m), 2.57–2.43 (4H, m), 2.10–2.04 (2H, m), 1.58–1.50 (2H, m); M/z(ES–)=505/507

Example 45
2-hydroxyethanesulfonic acid, N-[4-(4-chlorobenzenesulfonyl)-4-(2,5-difluorophenyl)-cyclohexyl]-amide

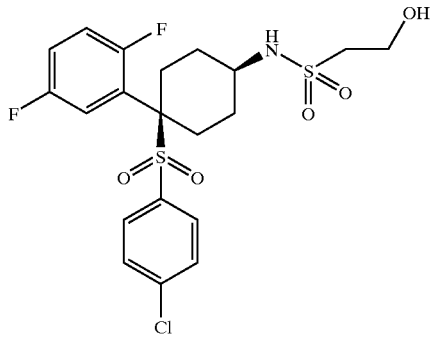

LiAlH$_4$ (0.29 ml of 1M solution in tetrahydrofuran, 0.29 mmol) in tetrahydrofuran (3 ml) at 0° C. under nitrogen was treated dropwise with a solution of the ester of Example 38 (50 mg, 0.1 mmol) in tetrahydrofuran (9 ml). The reaction mixture was stirred at ambient temperature for 3 days, quenched with aqueous sodium sulfate then partitioned between water and ethyl acetate. The combined organic layers were dried (MgSO$_4$) and evaporated to give a residue (47 mg) which was purified using preparative thin layer chromatography eluting with ethyl acetate:hexane 2:1 to give the desired product (12 mg). $^1$H NMR (CDCl$_3$) 7.38 (2H, d, J=9.2 Hz), 7.32 (2H, d, J=8.8 Hz), 7.08–7.04 (2H, m), 6.88–6.84 (1H, m), 5.39 (1H, d, J=6.4 Hz), 4.51–4.09 (2H, m), 3.65–3.63 (1H, m), 3.28 (2H, t, J=5.2 Hz), 2.83 (1H, t, J=5.6 Hz), 2.56–2.44 (4H, m), 2.05–2.20 (2H, m), 1.57–1.50 (2H, m); M/z(ES-)=492/494

Example 46
cyanomethanesulfonic acid, N-[4-(4-chlorobenzenesulfonyl)-4-(2,5-difluorophenyl)-cyclohexyl]-amide

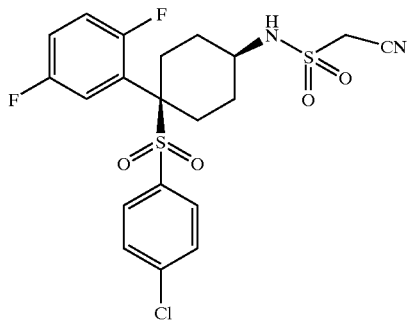

To a solution of the amide of Example 44 (80 mg, 0.16 mmol) in toluene (10 ml) under nitrogen was added thionyl chloride (23 μL, 0.32 mmol) and a catalytic amount of dimethylformamide. After refluxing for 16 h, the reaction was cooled to ambient temperature, diluted with water and extracted with ethyl acetate The combined organic layers were washed with brine, dried (MgSO$_4$) and evaporated to give a residue (78 mg) which was purified using preparative thin layer chromatography eluting with ethyl acetate:hexane 1:2 to give the desired product (42 mg). $^1$H NMR (CDCl$_3$) 7.39–7.31 (4H, m), 7.08–7.04 (2H, m), 6.88–6.84 (1H, m), 6.24 (1H, d, J=6.1 Hz), 4.12 (2H, s), 3.09–3.07 (1H, m), 2.62–2.46 (4H, m), 2.11–2.04 (2H, m), 1.65–1.57 (2H, m). M/z(ES-)=487/489

Example 47
trifluoromethanesulfonic acid, N-[4-(4-chlorobenzenesulfonyl)-4-(2,5-difluorophenyl)-cyclohexyl]-amide

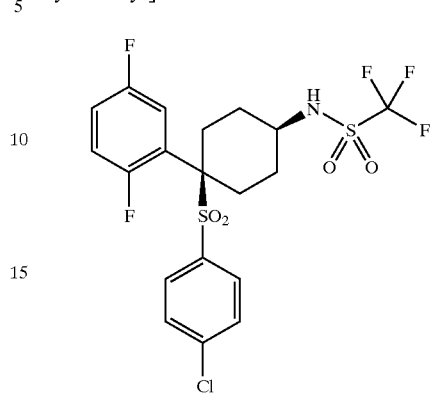

Intermediate A (110 mg, 0.29 mmol) in dichloromethane (3 ml) cooled to 0° C. was treated with triethylamine (99 μL, 0.43 mmol) followed by triflic anhydride (117 μL, 0.71 mmol). The reaction was stirred at 0° C. for 2.5 hours, slowly warming to ambient temperature, then diluted with ethyl acetate, washed with 2N sodium hydroxide, dried (MgSO$_4$) and evaporated to an orange oil which was purified by chromatography 15% ethyl acetate/hexane to yield a white solid (16 mg). $^1$H NMR (360 MHz, CDCl$_3$) δ 7.39–7.30 (4H, m), 7.09–7.04 (2H, m) 6.88–6.81 (1H, m), 5.86–5.84 (1H, m), 3.82–3.80 (1H, m), 2.64–2.42 (4H, m), 2.07–2.02 (2H, m), 1.66–1.59 (2H, m). m/z=540, 542[M+Na]$^+$

Example 48
methanesulfonic acid, N-[4-(4-chlorobenzenesulfonyl)-4-(2,5-difluorophenyl)-cyclohexyl]-N-methyl-amide

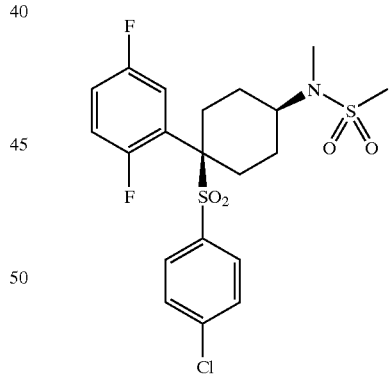

The product of Example 1 (52 mg, 0.11 mmol) in tetrahydrofuran (3 ml), cooled to 0° C. was treated with sodium hydride (11 mg, 0.28 mmol) After 10 minutes methyl iodide was added (70 μL, 1.1 mmol) and the reaction heated to 50° C. for 4 hours, then extracted into ethyl acetate and washed with H$_2$O, dried (MgSO$_4$) and evaporated. Product was purified by chromatography (25% ethyl acetate/hexane). $^1$H NMR (400 MHz, CDCl$_3$) δ 7.36–7.26 (4H, m), 7.04–7.01 (2H, m), 6.79–6.71 (1H, m), 3.91–3.84 (1H, m), 3.24–3.19 (2H, d, broad), 2.91 (3H, s), 2.86 (3H, s), 2.64–2.57 (2H, dd, J=12.5, J=3.8), 2.06–2.01 (2H, m), 1.85–1.76(2H, m). m/z= 500, 502 [MNa]$^+$

Example 49 methanesulfonic acid, N-[4-(2,5-difluorophenyl)-4-(4-trifluoromethyl-benzenesulfonyl)-cyclohexyl]-amide

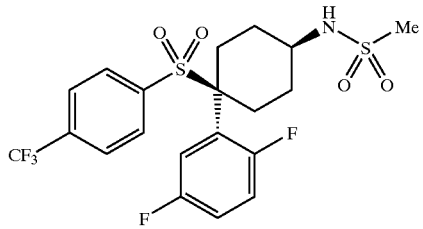

Intermediate B (150 mg, 0.36 mmol) was suspended in dry dichloromethane (5 ml) under nitrogen. Triethylamine (109 μl, 0.79 mmol) and methane sulfonyl chloride (42 μl, 0.54 mmol) were added and the reaction stirred for 16 h, diluted with dichloromethane, washed with water, brine, dried (MgSO$_4$) filtered and evaporated. The residue was purified by flash chromatography eluting with iso-hexane/ethyl acetate (1:1) to give a white solid (75 mg). $^1$H NMR δ (ppm) (CDCl$_3$): 1.53 (2H, m), 2.05 (2H, m), 2.48 (4H, m), 3.04 (3H, s), 3.64 (1H, m), 5.14 (1H, br), 6.84 (1H, m), 7.05 (2H, m), 7.54 (2H, d, J=7.8 Hz), 7.66 (2H, d, J=7.8 Hz). MS [MH$^+$] 499

The following examples were prepared by the same procedure, using the appropriate sulfonyl chloride:

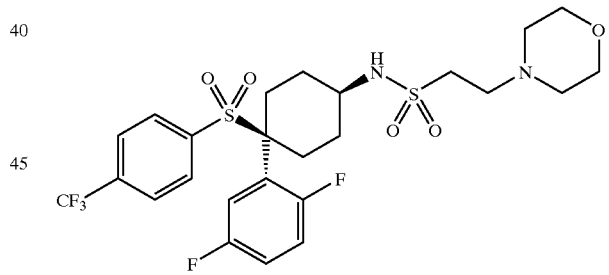

| Example | R | MS (MH$^-$) unless otherwise stated |
|---|---|---|
| 50 | 2-furyl | [MNa$^+$] 572 |
| 51 | ethyl | 513 |
| 52 | CH$_2$SO$_2$Me | [MNa$^+$] 598 |
| 53 | 4-methyl-1-methylimidazolyl | [MH$^+$] 564 |
| 54 | 5-isothiazolyl | [MH$^+$] 567 |
| 55 | 2-pyridyl | [MNa$^+$] 583, [MH$^+$] 561 |
| 56 | 5-chloro-2-thienyl | [MH$^+$] 600, 602 |
| 57 | n-propyl | [MH$^+$] 526 |
| 58 | 2-thienyl | [MH$^+$] 566. |
| 59 | 6-chloro-3-pyridyl | [MH$^+$] 596, 598 |
| 60 | 3-thienyl | [MH$^+$] 566 |
| 61* | vinyl | [MH$^+$] 510, [MH-SO$_2$Ar$^+$] 300 |

*- prepared using 2-chloroethanesulfonyl chloride. $^1$H NMR δ (ppm) (CDCl$_3$): 1.49–1.50(1H, m), 1.57–1.58(1H, m), 1.97–2.01(2H, m), 2.40–2.64(4H, m), 3.50–3.54(1H, m), 4.59(1H, dd, J=6.0, 0.7Hz), 5.95(1H, d, J=9.8Hz), 6.24(1H, d, J=9.8Hz), 6.53(1H, dd, J=9.7Hz, 6.8Hz) 6.79–6.86(1H, m), 7.04–7.10(2H, m), 7.52(2H, d, J=7.8Hz) 7.66(2H, d, J=7.8Hz).

Example 62 trifluoromethanesulfonic acid, N-[4-(2,5-difluorophenyl)-4-(4-trifluoromethyl-benzenesulfonyl)-cyclohexyl]-amide

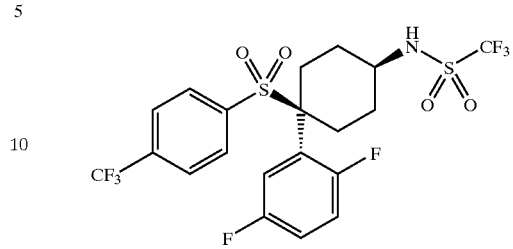

Intermediate B (170 mg, 0.41 mmol) in dry dichloromethane (5 ml) under nitrogen was treated at 0° C. with triethylamine (80 μl, 0.62 mmol) and triflic anhydride (133 μl, 0.82 mmol). The reaction was allowed to warm to room temperature, stirred for 3 h. diluted with dichloromethane, washed with water, brine, dried (MgSO$_4$) filtered and evaporated. The residue was purified by flash chromatography eluting with iso-hexane/ethyl acetate (1:1) to give a white solid (60 mg).

$^1$H NMR δ (ppm) (DMSO): 1.46–1.53 (2H, m), 1.81 (1H, s), 1.84 (1H, s), 2.41 (2H, t, J=13.1 Hz), 2.56–2.59 (1H, m), 2.59 (1H, d, J=2.7 Hz), 3.64 (1H, s), 7.10–7.23 (2H, m), 7.30–7.36 (1H, m), 7.60 (2H, d, J=8.2 Hz), 7.94 (2H, d, J=7.6 Hz), 9.77 (1H, d, J=7.6 Hz).

Example 63

2-(morpholin-4-yl)ethanesulfonic acid, N-[4-(2,5-difluorophenyl)-4-(4-trifluoromethyl-benzenesulfonyl)-cyclohexyl]-amide The vinyl sulfonamide of Example 61 (50 mg, 0.098 mmol) in dry dimethylformamide (3 ml) was treated with morpholine (130 μl, 1.47 mmol) and the reaction heated at 40° C. for 18 h, diluted with water, and extracted with ethyl acetate (×3). The combined organics were washed with water, brine, dried (MgSO$_4$), filtered and evaporated. The residue was purified by flash chromatography eluting with ethyl acetate and 1% triethylamine to give a white solid (28 mg).

$^1$H NMR δ (ppm) (CDCl$_3$): 1.53–1.61 (2H, m), 2.02–2.06 (2H, m), 2.49 –2.58 (8 H, m), 2.91 (2 H, t, J=6.5 Hz), 3.21 (2 H, t, J=6.5 Hz), 3.68–3.72 (1H, m), 3.77 (4 H, t, J=4.7 Hz), 5.55 (1 H, d, J=5.1 Hz), 6.83 (1 H, q, J=2.5 Hz), 7.05–7.09 (2 H, m), 7.52 (2 H, d, J=7.9 Hz), 7.65 (2 H, d, J=7.9 Hz). MS [MH$^+$] 597

Example 64

6-(morpholin-4-yl)pyridine-3-sulfonic acid, N-[4-(2,5-difluorophenyl)-4-(4-trifluoromethyl-benzenesulfonyl)-cyclohexyl]-amide

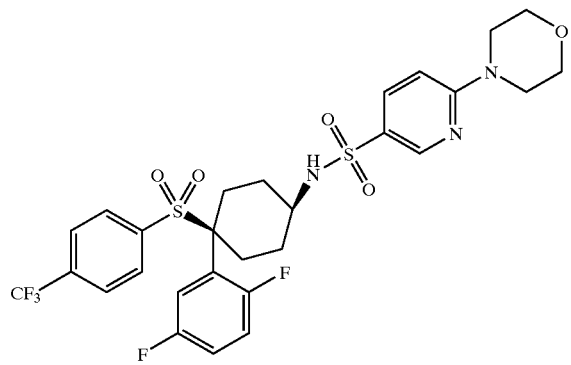

The product from example 59 (15 mg, 0.025 mmol) in ethanol (2 ml) was treated with morpholine (20 μL) and heated to reflux for 18 hours. The solvent was removed and the product purified by silica gel chromatography eluting the title compound with ethyl acetate/hexane mixtures, 16 mg. $^1$H NMR δ(ppm) (DMSO), 8.40 (1H, d, J=2.5 Hz), 7.94 (2H, d, J=8.1 Hz), 7.83 (1H, dd, J=2.5, 9.1 Hz), 7.71 (1H, d, J=4.6 Hz), 7.59 (2H, d, J=8.1 Hz), 7.26–7.33 (1H, m), 7.07–7.20 (2H, m), 6.93 (1H, d, J=9.1 Hz), 3.67–3.69 (8H, m), 2.50 (2H, m), 3.05 (1H, dd, J=1.9, 3.3 Hz), 2.30–2.37 (2H, m), 1.62–1.76 (2H, m) and 1.19–1.27 (2H, m).

Example 65

1,1-dimethylethanesulfinic acid, N-[4-(2,5-difluorophenyl)-4-(4-trifluoromethyl-benzenesulfonyl)-cyclohexyl]-amide

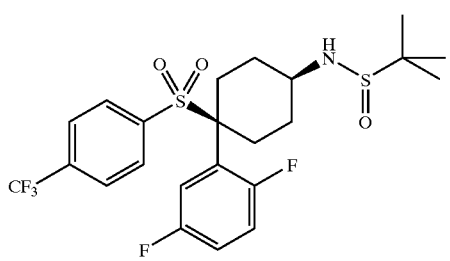

Intermediate B (0.73 g, 1.75 mmol) and 1,1-dimethylethyl sulfinamide (0.21 g, 1.75 mmol) in tetrahydrofuran (20 ml) was treated with titanium (IV) ethoxide (0.36 ml, 1.75 mmol) and heated to 80° C. for 18 hours. The reaction was quenched with water (0.35 ml) and stirred for 10 minutes before filtering through Celite™. The sulfinimine was cooled to −30° C. and treated with L-Selectride™ (1.75 ml, 1.0 mmol solution), and stirred for 2 hours whilst warming to −5° C. The reaction was then quenched with methanol (2 ml), and partitioned between ethyl acetate (50 ml) and brine (50 ml), dried (MgSO4) and evaporated to dryness. The product was purified by silica gel chromatography eluting with ethyl acetate/hexane mixtures. Yield 120 mg. $^1$H NMR δ(ppm) (CDCl$_3$), 7.68 (2H, d, J=7.5 Hz), 7.61 (2H, d, J=7.5 Hz), 7.05–7.15 (2H, m), 6.84–6.90 (1H, m), 3.56 (1H, q, J=2.7 Hz), 3.03 (1H, s), 2.62–2.42 (4H, m), 2.13–2.18 (1H, m), 1.83–1.76 (1H, m), 1.70–1.65 (1H, m), 1.50–1.40 (1H, m) and 1.24 (9 H, s). MS MH=524.

Example 66

1,1-dimethylethanesulfonic acid, N-[4-(2,5-difluorophenyl)-4-(4-trifluoromethyl-benzenesulfonyl)-cyclohexyl]-amide

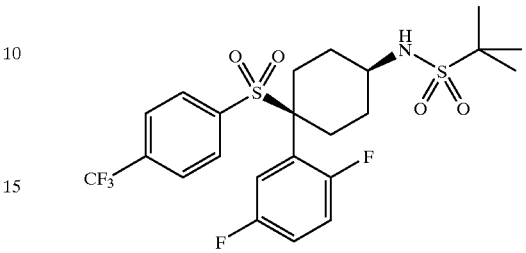

The product from Example 65 (110 mg, 0.21 mmol) in dichloromethane (2 ml) was treated with m-chloroperoxybenzoic acid (86 mg, 0.25 mmol, 50% w/w) and stirred for 1 hour. The reaction was diluted with dichloromethane (25 ml) and washed with sodium bisulfite (30 ml, 10% solution), saturated sodium bicarbonate (30 ml) and brine (20 ml), dried over magnesium sulfate, evaporated and purified by silica gel chromatography eluting the desired product with ethyl acetate/hexane mixtures, 80 mg. $^1$H NMR δ(ppm) (CDCl$_3$), 7.66 (2H, d, J=7.5 Hz), 7.53 (2H, d, J=7.5 Hz), 7.08–7.04 (2H, m), 6.90–6.78 (1H, m), 4.32 (1H, d, J=7.9 Hz), 3.64–3.55 (1H, m), 2.62–2.53 (2H, m), 2.48–2.38 (2H, m), 2.21–1.98 (2H, m), 1.65–1.54 (2H, m), 1.40 (9H, s), MS MH=540.

Example 67

2-(pyrrolidin-1-yl)ethanesulfonic acid, N-[4-(2,5-difluorophenyl)-4-(4-trifluoromethyl-benzenesulfonyl)-cyclohexyl]-amide

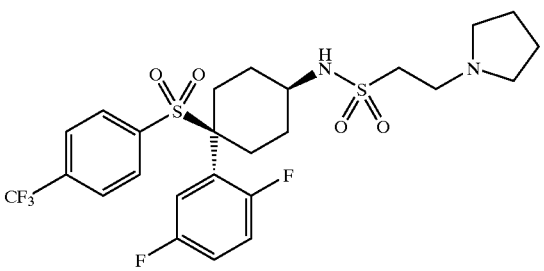

To the vinyl sulfonamide prepared in example 61 (100 mg, 0.19 mmol) in dry dimethylformamide (3 ml) was added pyrrolidine (0.25 ml, 2.49 mmol). The reaction was heated at 40° C. for 4 h, diluted with water, and extracted with ethyl acetate (×3). The combined organics were washed with water, brine, dried (MgSO$_4$), filtered and evaporated. The residue was purified by flash chromatography eluting with dichloromethane/methanol (9:1) to give a white solid (60 mg). MS [MH$^+$] 581

Example 68

3-{[4-(2,5-difluorophenyl)-4-(4-trifluoromethylbenzenesulfonyl)-cyclohexyl]aminosulfonyl}-thiophene-2-carboxylic acid, methyl ester

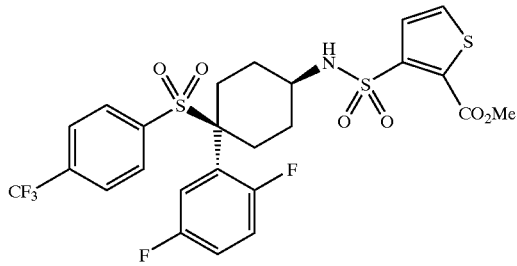

Prepared from Intermediate B (200 mg, 0.48 mmol) by the procedure of Example 49. The product was purified by flash chromatography eluting with iso-hexane/ethyl acetate (3:1) to give a white solid (125 mg).

$^1$H NMR δ (ppm) (CDCl$_3$): 1.34–1.43 (2H, m), 1.84–1.88 (2H, m), 2.33–2.55 (4H, m), 3.49 (1H, dd, J=3.0, 5.4 Hz), 4.03 (3H, s), 6.72 (1H, d, J=6.0 Hz), 6.76–6.83 (1H, m), 6.98–7.07 (2H, m), 7.51–7.57 (4H, m), 7.65–7.67 (2H, d, J=7.8 Hz).

Examples 69–73

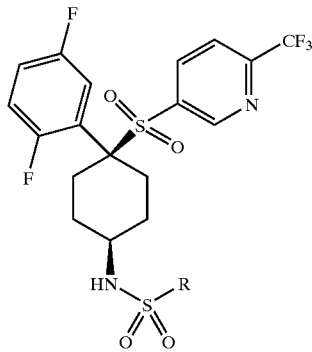

The following sulfonamides were prepared by the procedure of Example 1 using Intermediate C and the appropriate sulfonyl chloride.

| Example | R | MS (MH$^+$) |
| --- | --- | --- |
| 69 | methyl | 499 |
| 70 | 2-thienyl | 567 |
| 71 | 5-isothiazolyl | 568 |
| 72 | n-propyl | 527 |
| 73* | 2-chloro-2-propyl | 561, 563 |

*Isopropylsulfonyl chloride was used.

Example 74 trifluoromethanesulfonic acid, N-[4-(2,5-difluorophenyl)-4-(6-trifluoromethyl-pyridine-3-sulfonyl)-cyclohexyl]-amide

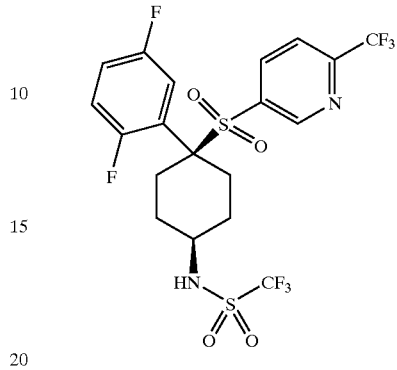

Intermediate C (100 mg) in dichloromethane (5 ml) and treated with triethylamine (1 equivalent) and cooled to −78° C. Trifluoromethanesulfonic anhydride (2 equivalents) was added, the reaction mixture warmed to −40° C. and stirred at this temperature for 3 h. The mixture was quenched with aqueous citric acid, diluted with ethyl acetate and warmed to room temperature. The organic phase was separated, washed with brine, dried (MgSO$_4$), filtered and evaporated in vacuo. Purification by column chromatography (eluting with 5/1 hexane/ethyl acetate) gave the title compound (120 mg, 91%) as a white powder. $^1$H NMR (CDCl$_3$, 400 MHz) 8.60 (1H, d, J=1.9), 7.91 (1H, dd, J=8.2, 1.9), 7.74 (1H, d, J=8.2), 7.26–7.10 (2H, m), 6.88–6.81 (1H, m), 5.70 (1H, brd, J=5), 3.83 (1H, brs), 2.64–2.48 (4H, m), 2.11–2.07 (2H, m), 1.70–1.65 (2H, m).

Example 75 trifluoromethanesulfonic acid, N-[4-(5-bromo-2-fluorophenyl)-4-(6-trifluoromethyl-pyridine-3-sulfonyl)-cyclohexyl]-amide

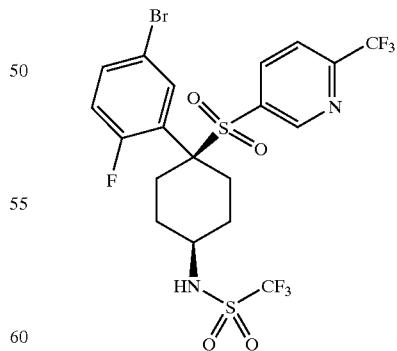

Prepared by the procedures of Intermediate C (using 2-fluoro-5-bromobenzyl bromide in Step 2) and Example 1 (using trifluoromethanesulfonyl chloride). M/Z=613, 615 (MH$^+$).

Example 76 trifluoromethanesulfonic acid, N-[4-(5-cyano-2-fluorophenyl)-4-(6-trifluoromethyl-pyridine-3-sulfonyl)-cyclohexyl]-amide

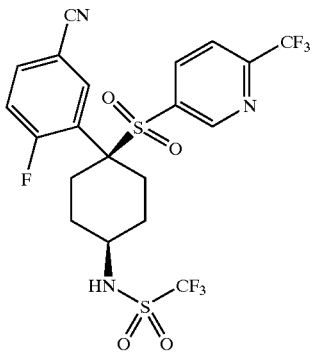

A solution of the compound prepared in Example 75 (45 mg) was treated with copper cyanide (4 equivalents), pyridine (1 drop) and dimethylformamide (3 ml) and heated at 180° C. overnight. The reaction was diluted with ethyl acetate and water and filtered. The organic layer of the filtrate was washed with water and brine and dried, filtered and evaporated in vacuo. Purification by column chromatography gave the nitrile (27 mg, 66%). M/Z=559 (MH$^+$).

Example 77 trifluoromethanesulfonic acid, N-[4-(2-fluoro-5-methyl-phenyl)-4-(6-trifluoromethyl-pyridine-3-sulfonyl)-cyclohexyl]-amide

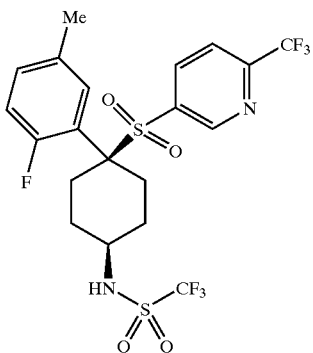

The compound prepared in Example 75 (50 mg) in dioxane was treated with cesium fluoride (2.2 equivalents), tri-tert-butylphosphine (12 mol %), tetramethyltin (2 equivalents), and Pd$_2$(dba)$_3$ (3 mol %) and heated at 100° C. for 3 h. The reaction mixture was cooled, diluted with ether, filtered and the filtrate evaporated in vacuo. Purification by column chromatography gave the toluene derivative (13 mg, 29%).

M/Z =549 (MH$^+$).

Example 78 trifluoromethanesulfonic acid, N-[4-(2-fluoro-5-(hydroxymethyl)-phenyl)-4-(6-trifluoromethyl-pyridine-3-sulfonyl)-cyclohexyl]-amide

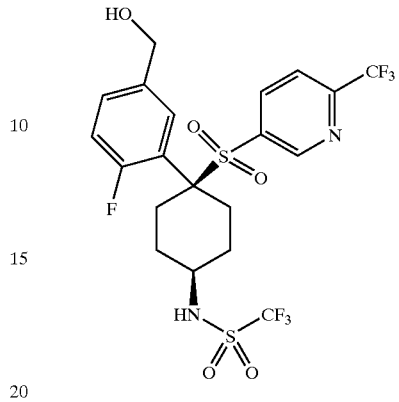

(1) A solution of the compound prepared in Example 75 (50 mg) in dioxane was treated with CsF (2.2 equivalents), tri-tert-butylphosphine (12 mol %), tributylvinyltin (2 equivalents), and Pd$_2$(dba)$_3$ (3 mol %) and heated at 100° C. for 2 h. The reaction mixture was cooled, diluted with ether, filtered and the filtrate evaporated in vacuo. Purification by column chromatography gave the styrene (30 mg).

(2) A solution of the foregoing styrene in dichloromethane (4 ml) and methanol (1 ml) was cooled to −78° C. and treated with excess ozone. The reaction mixture was quenched with dimethyl sulfide, warmed to room temperature and evaporated in vacuo to give the crude aldehyde.

(3) A solution of the foregoing aldehyde in ethanol (3 ml) was cooled to −78° C. and treated with sodium borohydride (2 equivalents) and stirred for 3 h. The reaction mixture was quenched with citric acid, warmed to room temperature and diluted with ethyl acetate. The organic layer was washed with water and brine, dried (MgSO4), filtered and evaporated. Purification by column chromatography gave the alcohol (16 mg, 53%).
M/Z=547 (M−OH+H$^+$).

Example 79 trifluoromethanesulfonic acid, N-[4-(2,5-difluorophenyl)-4-(4-vinylbenzenesulfonyl)-cyclohexyl]-amide

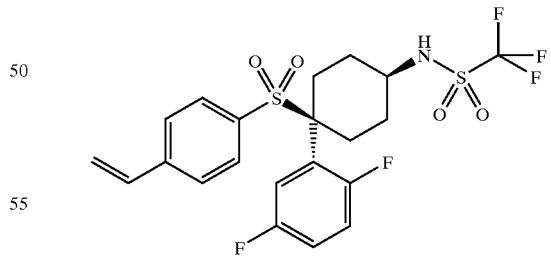

Nitrogen was bubbled through a solution containing the product of Example 47 (1.0 g, 1.93 mmol), tri-t-butylphosphine (0.1 M in dioxane, 190 μl, 0.19 mmol), cesium fluoride (0.65 g, 4.28 mmol) and Pd$_2$(dba)$_3$ (0.10 g, 0.11 mmol) in dioxane (8 ml) in a sealed tube for 5 minutes. Tributyl(vinyl)tin (0.65 g, 2.05 mmol) was added and the mixture heated at 100° C. for 2 hours. This sequence was repeated on the same scale a further four times. All five reaction mixtures were combined and diluted with diethyl ether (50 ml) and filtered through a silica gel pad, evaporated in vacuo to give crude product which was chromatographed on silica eluting with 5–20% ethyl acetate/isohexane, then azeotroped with dichloromethane to give the desired product (2.67 g, 55%). ¹H NMR (CDCl₃, 360 MHz): 1.59–1.70 (2H, m), 2.02–2.06 (2H, m), 2.44 (2H, t, J=12.7 Hz), 2.61–2.65 (2H, m), 3.78 (1H, m), 5.47 (1H, d, J=10.9 Hz), 5.82 (1H, bd, J=7.8 Hz), 5.88 (1H, d, J=17.5 Hz), 6.68–6.87 (1H, m), 7.01–7.08 (2H, m), 7.32 (2H, d, J=8.3), 7.40 (2H, d, J=8.1), 10.10 (1H, s)

Example 80
trifluoromethanesulfonic acid, N-[4-(2,5-difluorophenyl)-4-(4-formylbenzenesulfonyl)-cyclohexyl]-amide

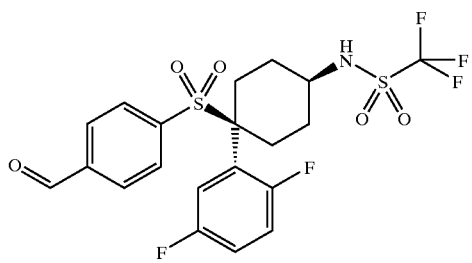

Ozone was bubbled through a solution of the product of Example 79 (2.5 g, 4.9 mmol) in dichloromethane/methanol (125 ml/25 ml) at −78° C. until a blue colour was observed. Oxygen was bubbled through the mixture for 10 minutes until the blue colour disappeared. The mixture was quenched with dimethyl sulfide (2.16 ml, 29.5 mmol), allowed to warm to room temperature and stirred for 16 hours. The mixture was concentrated in vacuo to give an oil (2.80 g), which was chromatographed on silica, eluting with 20% ethyl acetate/isohexane to give the aldehyde (2.18 g, 87%). ¹H NMR (CDCl₃, 360 MHz): 1.59–1.70 (2H, m), 2.04–2.09 (2H, m), 2.48 (2H, t, J=12.3), 2.61–2.68 (2H, m), 3.82 (1H, m), 5.75 (1H, d, J=7.7), 6.77–6.86 (1H, m), 7.07–7.11 (2H, m), 7.57 (2H, d, J=8.1), 7.90 (2H, d, J=8.3), 10.10 (1H, s)

Example 81
4-{1-(2,5-difluorophenyl)-4-[(trifluoromethanesulfonyl)amino]-cyclohexanesulfonyl}-benzaldehyde oxime

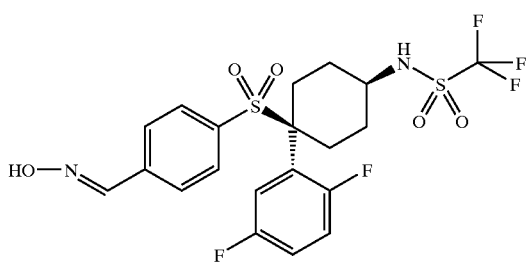

A solution of the product of Example 80 (0.40 g, 0.80 mmol), hydroxylamine hydrochloride (0.16 g, 2.4 mmol) and sodium acetate (0.19 g, 2.4 mmol) in ethanol (60 ml) was heated at reflux for 16 hours and stirred at room temperature for 32 hours. The mixture was evaporated in vacuo and extracted with ethyl acetate (50 ml). The organic phase was washed with brine (sat. 40 ml), dried (magnesium sulfate) and evaporated in vacuo. The crude product was chromatographed on silica, eluting with 20–28% ethyl acetate/isohexane to give the oxime (0.36 g, 87%). ¹H NMR (DMSO, 360 MHz): 1.49 (2H, bt, J=12.3), 1.82 (2H, bd, J=14.0), 2.40 (2H, bt, J=13.8), 2.50–2.60 (2H, m), 3.64 (1H, bs), 7.08–7.20 (2H, m), 7.28–7.34 (1H, m), 7.37 (2H, d, J=8.3), 7.72 (2H, d, J=8.3), 8.24 (1H, s), 9.76 (0.5H, d, J=5.9), 11.74 (0.5H, s)

Example 82
trifluoromethanesulfonic acid, N-[4-(2,5-difluorophenyl)-4-(4-(fluoromethyl)benzenesulfonyl)-cyclohexyl]-amide

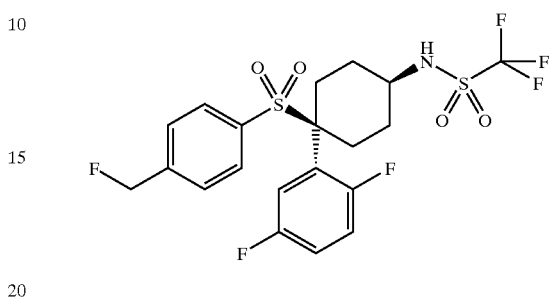

Sodium borohydride (0.89 g, 2.3 mmol) was added to a solution of the product from Example 80 (0.40 g, 0.8 mmol) in dry tetrahydrofuran (20 ml) at 0° C. The mixture was stirred at room temperature for 48 hours, extracted with ethyl acetate (30 ml), the organic layer washed with water (30 ml) and brine (sat. 30 ml), dried (magnesium sulfate) and evaporated in vacuo to give crude product (0.43 g). This was chromatographed on silica, eluting with 40% ethyl acetate/isohexane to give the benzyl alcohol (0.25 g, 61%). ¹H NMR (CDCl₃, 360 MHz): 1.67–1.61 (2H, m), 1.94 (1H, t, J=5.7), 2.02–2.05 (2H, m), 2.43 (2H, bt, J=13.4), 2.62 (2H, bd, J=13.6), 3.80 (1H, bs), 4.81 (2H, d, J=5.2), 5.70 (1H, bs), 6.80–6.87 (1H, m), 6.99–7.07 (2H, m), 7.39 (4H, m)

Diethylaminosulfur trifluoride (50 μl, 0.4 mmol) in dry dichloromethane (1.0 ml) was added to a solution of the aforesaid benzyl alcohol (0.1 g, 0.2 mmol) in dry dichloromethane (1.0 ml) at −78° C. The mixture was allowed to warm to room temperature, stirred for 16 hours, and evaporated in vacuo. The crude product was chromatographed on silica, eluting with 20% ethyl acetate/isohexane to give the benzyl fluoride (0.85 g, 83%). ¹H NMR (CDCl₃, 360 MHz): 1.59–1.68 (2H, m), 2.03–2.06 (2H, m), 2.44 (2H, bt, J=13.1), 2.62 (2H, bd, J=12.2), 3.79–3.82 (1H, m), 5.30 (1H, s), 5.40 (1H, s), 5.63 (1H, d, J=8.4), 6.83 (1H, m), 7.02–7.06 (2H, m), 7.37–7.43 (4H, m)

Example 83
trifluoromethanesulfonic acid, N-[4-(2,5-difluorophenyl)-4-(4-(difluoromethyl)benzenesulfonyl)-cyclohexyl]-amide

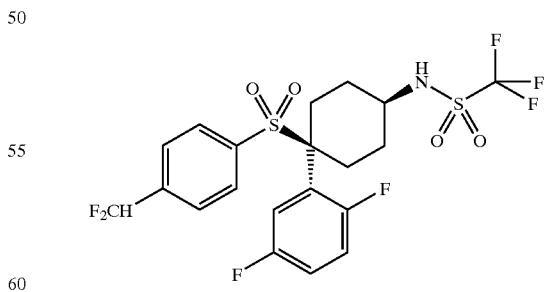

Diethylaminosulfur trifluoride (0.10 g, 0.65 mmol) was added to a solution of the product from Example 80 (0.2 g, 0.40 mmol) in dry dichloromethane (2 ml). After stirring for 90 hours at room temperature, the mixture was diluted with water (10 ml). The organic phase was washed with water (10 ml), dried (magnesium sulfate) and evaporated in vacuo to give an oil. The crude product was chromatographed on silica, eluting with 20% ethyl acetate/isohexane to give the difluoride (0.17 g, 80%). $^1$H NMR (CDCl$_3$, 400 MHz): 1.59–1.68 (2H, m), 2.06 (2H, dd, J=3.2 and J=14.4), 2.45 (2H, bt, J=13.2), 2.62 (2H, bd, J=14.1), 3.78–3.83 (1H, m), 5.51 (1H, d, J=8.3), 6.69 (1H, t, J=55.8), 6.79–6.86 (1H, m), 7.04–7.09 (2H, m), 7.49 (2H, d, J=8.5), 7.55 (2H, d, J=8.4)

Example 84 trifluoromethanesulfonic acid, N-[4-(4-cyanobenzenesulfonyl)-4-(2,5-difluorophenyl)-cyclohexyl]-amide

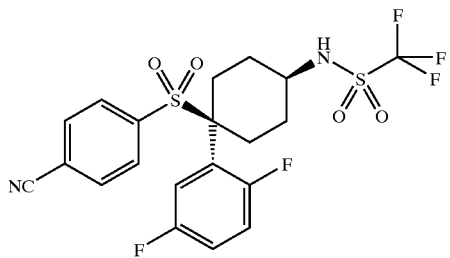

Triphenyl phosphine (0.32 g, 1.2 mmol), followed by carbon tetrachloride (0.06 ml, 0.60 mmol), were added to a solution of the product from Example 80 (0.16 g, 0.30 mmol) in acetonitrile (1.5 ml). The mixture was stirred for 1.5 hours, additional carbon tetrachloride (0.18 ml, 0.18 mmol) was added, and the mixture was stirred for 0.5 hours, diluted with water (10 ml) and extracted with diethyl ether (2×10 ml). The combined organic phases were washed with brine (sat. 20 ml), dried (magnesium sulfate) and evaporated in vacuo. The crude product was chromatographed on silica, eluting with 20% ethyl acetate/isohexane to give the nitrile (0.11 g, 71%). $^1$H NMR (CDCl$_3$, 360 MHz): 1.63–1.69 (2H, m), 2.04–2.09 (2H, m), 2.48 (2H, bt, J=13.0), 2.59–2.64 (2H, m), 3.81 (1H, m), 5.66 (1H, d, J=7.3), 6.79–6.86 (1H, m), 7.07–7.13 (2H, m), 7.52 (2H, d, J=8.5), 7.70 (2H, d, J=8.5)

Example 85 trifluoromethanesulfonic acid, N-[4-(benzenesulfonyl)-4-(2,5-difluorophenyl)-cyclohexyl]-amide

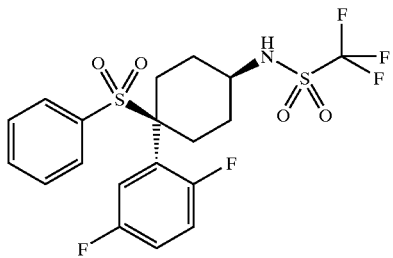

A solution of the product from Example 47 (0.28 g, 0.6 mmol) was flushed with nitrogen, 10% palladium on carbon (0.03 g, 10% w/w) was added, and the mixture was hydrogenated at 40 psi for 16 hours. Filtration and evaporation in vacuo gave the product (0.28 g, 99%). $^1$H NMR (CDCl$_3$, 400 MHz): 1.61–1.68 (2H, m), 2.03–2.07 (2H, m), 2.44 (2H, bt, J=13.2), 2.63 (2H, bd, J=13.5), 3.78–3.82 (1H, m), 5.64 (1H, d, J=8.4), 6.78–6.85 (1H, m), 6.99–7.08 (2H, m), 7.38–7.43 (4H, m), 7.60–7.65 (1H, m).

What is claimed is:

1. A compound of formula I:

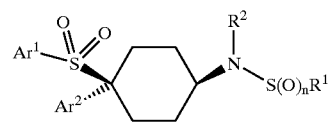

wherein n is 1 or 2;

$R^1$ represents CF$_3$ or C$_{1-6}$alkyl, C$_{2-6}$alkenyl, C$_{3-9}$cycloalkyl or C$_{3-6}$cycloalkylC$_{1-6}$alkyl, any of which may bear up to 2 substituents selected from halogen, CN, CF$_3$, OR$^3$, COR$^3$, CO$_2$R$^3$, OCOR$^4$, SO$_2$R$^4$, N(R$^5$)$_2$, and CON(R$^5$)$_2$, or R$^1$ represents aryl, arylC$_{1-6}$alkyl, C-heterocyclyl or C-heterocyclylC$_{1-6}$alkyl;

R$^2$ represents H or C$_{1-4}$alkyl;

R$^3$ represents H, C$_{1-4}$alkyl, phenyl or heteroaryl;

R$^4$ represents C$_{1-4}$alkyl, phenyl or heteroaryl;

R$^5$ represents H or C$_{1-4}$alkyl, or two R$^5$ groups together with a nitrogen atom to which they are mutually attached complete an azetidine, pyrrolidine, piperidine, morpholine, thiomorpholine or thiomorpholine-1,1-dioxide ring;

Ar$^1$ and Ar$^2$ independently represent phenyl or heteroaryl, either of which bears 0–3 substituents independently selected from halogen, CN, NO$_2$, CF$_3$, CHF$_2$, OH, OCF$_3$, CHO, CH=NOH, C$_{1-4}$alkoxy, C$_{1-4}$alkoxycarbonyl, C$_{2-6}$acyl, C$_{2-6}$alkenyl and C$_{1-4}$alkyl which optionally bears a substituent selected from halogen, CN, NO$_2$, CF$_3$, OH and C$_{1-4}$alkoxy;

aryl at every occurrence thereof refers to phenyl or heteroaryl which optionally bear up to 3 substituents selected from halogen, CN, NO$_2$, CF$_3$, OCF$_3$, OR$^3$, COR$^3$, CO$_2$R$^3$, OCOR$^4$, N(R$^5$)$_2$, CON(R$^5$)$_2$ and optionally-substituted C$_{1-6}$alkyl, C$_{1-6}$alkoxy, C$_{2-6}$alkenyl or C$_{2-6}$alkenyloxy wherein the substituent is selected from halogen, CN, CF$_3$, phenyl, OR$^3$, CO$_2$R$^3$, OCOR$^4$, N(R$^5$)$_2$ and CON(R$^5$)$_2$; and C-heterocyclyl and N-heterocyclyl at every occurrence thereof refer respectively to a heterocyclic ring system bonded through carbon or nitrogen, said ring system being non-aromatic and comprising up to 10 atoms, at least one of which is O, N or S, and optionally bearing up to 3 substituents selected from oxo, halogen, CN, NO$_2$, CF$_3$, OCF$_3$, OR$^3$, COR$^3$, CO$_2$R$^3$, OCOR$^4$, OSO$_2$R$^4$, N(R$^5$)$_2$, CON(R$^5$)$_2$ and optionally-substituted phenyl, C$_{1-6}$alkyl, C$_{1-6}$alkoxy, C$_{2-6}$alkenyl or C$_{2-6}$alkenyloxy wherein the substituent is selected from halogen, CN, CF$_3$, OR$^3$, CO$_2$R$^3$, OCOR$^4$, N(R$^5$)$_2$ and CON(R$^5$)$_2$;

or a pharmaceutically acceptable salt thereof.

2. A compound according to claim 1 wherein Ar$^1$ is 6-trifluoromethyl-3-pyridyl, 4-chlorophenyl or 4-trifluoromethylphenyl and Ar$^2$ is 2,5-difluorophenyl.

3. A compound according to claim 1 of formula II:

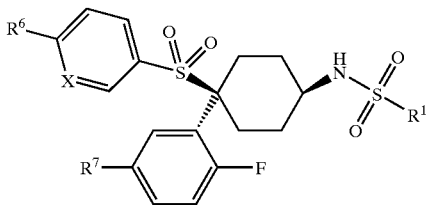

wherein X represents N or CH;

$R^6$ represents H, F, Cl, Br, CN, $CF_3$, $CH=CH_2$ or $CH_3$;

$R^7$ represents F, Cl, Br, CN, $CH_3$ or $CH_2OH$; and $R^1$ is as defined in claim 1;

or a pharmaceutically acceptable salt thereof.

4. A compound according to claim 3 wherein $R^1$ is $CF_3$.

5. The compound according to claim 4 which is trifluoromethanesulfonic acid, N-[4-(2,5-difluorophenyl)-4-(6-trifluoromethyl-pyridine-3-sulfonyl)-cyclohexyl]-amide or a pharmaceutically acceptable salt thereof.

6. A pharmaceutical composition comprising a compound according to claim 1 or a pharmaceutically acceptable salt thereof and a pharmaceutically acceptable carrier.

7. A method of treatment of a subject suffering from or prone to a condition associated with the deposition of β-amyloid which comprises administering to the subject an effective amount of a compound according to claim 1 or a pharmaceutically acceptable salt thereof.

8. The method according to claim 7 wherein the condition is Alzheimer's disease.

9. A process for preparing a compound according to claim 1 in which $R^2$ is H comprising reacting a sulfinylchloride $R^1SOCl$ or a sulfonyl chloride $R^1SO_2Cl$ or a sulfonic anhydride $(R^1SO_2)_2O$ with an amine of formula III:

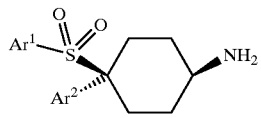

wherein $R^1$, $Ar^1$ and $Ar^2$ are as defined in claim 1.

* * * * *